United States Patent [19]
Schmiesing et al.

[11] Patent Number: 5,634,465
[45] Date of Patent: Jun. 3, 1997

[54] CONTINUOUS DISPLAY OF CARDIAC BLOOD FLOW INFORMATION

[75] Inventors: Daniel C. Schmiesing, Bothell; Helen F. Routh, Seattle; Bruce A. Kincy; Marshall T. Robinson, both of Snohomish, all of Wash.

[73] Assignee: Advanced Technology Laboratories, Inc., Bothell, Wash.

[21] Appl. No.: 489,258

[22] Filed: Jun. 9, 1995

[51] Int. Cl.$^6$ .................................. A61B 8/06; G01F 1/00
[52] U.S. Cl. .................................. 128/661.08; 73/861.25
[58] Field of Search ............................ 128/661.09, 661.1; 73/861.25

[56] References Cited

U.S. PATENT DOCUMENTS

| | | | |
|---|---|---|---|
| 4,509,525 | 4/1985 | Seo | 128/663 |
| 4,608,993 | 9/1986 | Albert | 128/663 |
| 4,848,354 | 7/1989 | Angelsen et al. | 128/660 |
| 4,850,364 | 7/1989 | Leavitt | 128/661 |
| 4,866,613 | 9/1989 | Amemiya et al. | 364/413 |
| 5,065,764 | 11/1991 | Nakamura et al. | 128/661 |
| 5,271,404 | 12/1993 | Corl et al. | 128/661.08 |
| 5,280,787 | 1/1994 | Wilson et al. | 128/661 |
| 5,287,753 | 2/1994 | Routh et al. | 73/861 |
| 5,450,850 | 9/1995 | Iinuma | 128/661.09 |
| 5,462,059 | 10/1995 | Ferrara et al. | 128/661.09 |

OTHER PUBLICATIONS

*Doppler Ultrasound*, Evans et al., Wiley & Sons (1989), pp. 166–184.
R.W. Gill, Ult. in Med. & Biol., vol.5 at pp. 237–247 (1979).
Gerzberg & Meindl, Ultrasonic Imaging, vol.2 at pp. 232–261 (1980).
L.Y.L. Mo et al., Ult in Med & Biol., vol.14, No.5 at pp. 355–363 (1988).
Gerzberg & Meindl, Ultrasonic Imaging, vol.2 at pp. 262–289 (1980).

*Primary Examiner*—Francis Jaworski
*Attorney, Agent, or Firm*—W. Brinton Yorks, Jr.

[57] ABSTRACT

A technique for continuously determining and displaying the peak velocities of spectral Doppler information is disclosed. A Doppler noise threshold level is determined from operating characteristics of the ultrasound system, probe, or both. Received spectral Doppler data for a spectral line is compared to this threshold to identify a valid peak velocity value. Spectral lines are examined in advance of their display to detect excursions due to artifacts such as valve clicks. Peak velocity values are interpolated and displayed in place of artifact peak values. Individual heart cycles over which quantified measures of cardiovascular performance are computed and displayed are selected by the R-wave intervals of an ECG trace. The interval of the concurrent spectral Doppler display corresponding to the heart cycle interval over which the quantified measures are computed or pertain is automatically highlighted for the user.

25 Claims, 6 Drawing Sheets

CONTINUOUS DISPLAY OF CARDIAC BLOOD FLOW INFORMATION

This invention relates to ultrasonic diagnostic systems which measure blood flow characteristics of the heart by Doppler techniques and, in particular, to the continuous display of such information including peak and mean blood flow velocities.

In the ultrasonic measurement of blood flow characteristics, waves of returning ultrasonic signals are compared to a phase reference to determine the phase shift of the returning waves. As the transmitted ultrasonic wave impinges upon flowing material such as blood cells, the movement of the flowing material will impart a Doppler shift to the returning echo signal. This frequency shift, which is commonly measured in kilohertz, translates into the rate of movement or velocity of the blood flow. Doppler velocity information is conventionally displayed as a continuous spectrum of lines of varying amplitudes in a moving or scrolled display on a video monitor. Each line represents an instantaneous measurement of blood flow velocities. As the flow of blood in a vessel or the heart is continuously monitored and interrogated by Doppler ultrasound, the spectrum of systolic and diastolic velocities is continuously displayed and passed before the clinician.

In order to analyze the various disease states of the cardiovascular system it is desirable to calculate a number of parameters from the spectral velocity information. These parameters include, inter alia, peak blood flow velocity, peak pressure gradient, the velocity time integral, the time averaged peak velocity, and mean pressure gradient. Many of these parameters are predicated upon identifying peak velocities of blood flow. The conventional technique for determining peak velocities and related parameters is to save a recording of a period of spectral information over several consecutive heart cycles. With the spectral display held motionless on the screen the clinician manually traces the peaks of the spectral display with a cursor. Calculation software may then use the spectral tracing to calculate mean velocities and a variety of other parameters.

This technique has several obvious disadvantages including the need to do a tedious, time consuming tracing and the inaccuracies inherent in a manually executed procedure. Moreover, this technique does not lend itself to automated processing, as the calculation software is dependent upon this manual exercise of display tracing. Furthermore, the ultrasonic examination of a patient must be interrupted by stopping the acquisition of Doppler information in order to perform the manual tracing of previously acquired data. It would be preferable to be able to automatically acquire the peak and mean velocity data without the need for manual intervention or interruption of a patient examination.

An improved ultrasonic Doppler display is described in U.S. Pat. No. 5,287,753, which discloses a technique for continuously determining and displaying the peak and mean velocities of spectral Doppler information. Received spectral Doppler data is examined over a predetermined period to determine a noise threshold level. Individual instantaneous measurements, or lines, of Doppler spectral information are analyzed to compare the line information against the noise threshold. The correlation of the threshold and the spectral line information identifies the peak velocity of the spectral line. Mean velocity is calculated as an intensity weighted mean of the spectral line information. The identified peak and mean velocities are displayed in contrasting colors or shades on a continuously updated and displayed frequency versus time spectral display.

While the ultrasonic apparatus of this patent has been found to perform admirably in diagnosing conditions throughout most of the cardiovascular system, the heart presents several unique problems and challenges. Spectral information derived from the heart can be contaminated with signal components originating with rapidly moving heart tissue such as the valves of the heart. Artifacts resulting from this valve motion, commonly known as valve clicks, can appear at varying times in the cyclic spectral data, and at varying times and frequencies depending on the sampling site, type of valve and disease state. It would be desirable to automatically remove the valve click artifacts from the real time spectral data prior to its display on the monitor. Furthermore, it is desirable to identify characteristics of the spectral information such as peak flow velocities even in the presence of randomly occurring, varying amplitude valve click artifacts. Moreover it is desirable to identify peak velocities immediately in real time so that displayed spectral information will always portray peak velocity characteristics.

In accordance with the principles of the present invention, received Doppler information is compared against a noise threshold to accurately determine peak blood flow velocity. The noise threshold is a function of predetermined system parameters, enabling the noise threshold to be determined prior to the receipt of patient Doppler information. Received Doppler information can then be compared immediately against the threshold to ascertain peak blood flow velocities without an initial calibration delay.

In accordance with a further aspect of the present invention, valve click artifacts are detected in spectral Doppler data and their effects eliminated from peak velocity identification by examining the data of a number of spectral lines for such artifacts prior to their display. The onset and termination of the artifacts are detected by an excessive increment and decrement in the number of discrete Doppler gradations over a predetermined number of lines. When these excessive increments and decrements are detected, the effect of the artifact is eliminated by displaying interpolated values between the times of the successive increment and decrement.

In accordance with yet another aspect of the present invention, the duration of a cardiac cycle is determined by identifying the period of a cardiac cycle from a measured R-wave of the heart. The peak blood flow velocity occurring during the heart cycle is then ascertained as the first major peak in the spectral display which follows the occurrence of the R-wave. Quantified blood flow characteristics are calculated from the Doppler signals of identified heart cycles, and the spectral lines corresponding to the Doppler signals from which the quantified measures are calculated are automatically highlighted in the spectral display.

IN THE DRAWINGS

Figure 1:
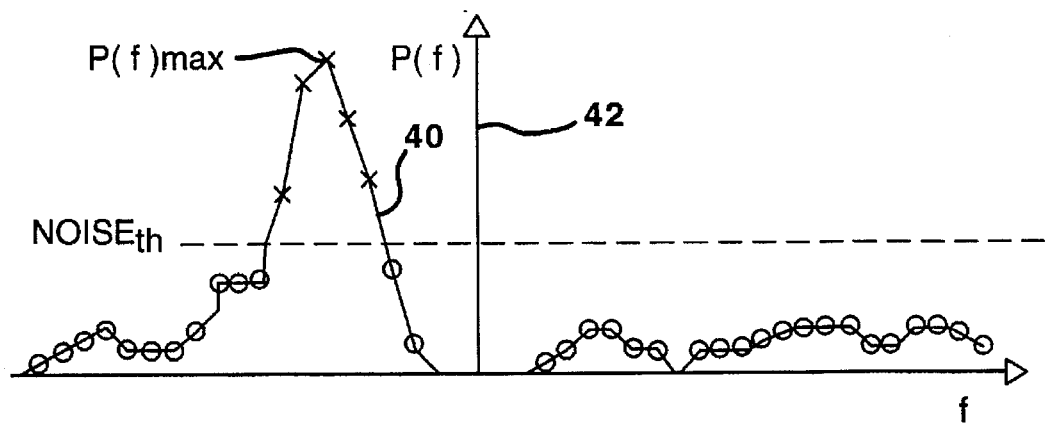
FIG. 1 illustrates an intensity versus frequency plot of the data points of a typical Doppler spectral measurement.

FIG. 1 illustrates an intensity versus frequency plot of Doppler data produced by a cardiac ultrasound system's Doppler processor from signals acquired during a particular time of Doppler interrogation of the blood flow in a vessel or organ being examined. FIG. 1 is also discussed in U.S. patent application Ser. No. 892,301, now U.S. Pat. No. 5,287,753, the contents of which is hereby fully incorporated by reference. In a digital signal processing system such as the HDI 3000cv system manufactured by the assignee of the present invention the Doppler data is a series of discrete digital values as denoted by the circles and X's of FIG. 1. For ease of illustration a curve 40 in FIG. 1 has been drawn to connect the digital values. The curve 40 and its digital values will range about a vertical axis 42, extending over a range of frequency values in the horizontal direction. The vertical axis 42 marks a frequency value of zero on the horizontal frequency axis. The frequency limits vary with the system setting for the range of velocities to be detected. Exemplary limits might be +10,000 Hz and −10,000 Hz, which can correspond to flow velocities of +3.85 m/sec and −3.85 m/sec, respectively. In the vertical intensity direction the point P(f)max denotes the maximum power or intensity of the received signals at its corresponding frequency on the horizontal frequency axis. The frequency of peak power is not the peak signal frequency, however, which it is an objective of the present invention to identify.

To positively identify the peak signal frequency, valid Doppler signals must be distinguished from noise. Without a viable noise immunity technique, a peak signal tracing technique can erroneously identify noise peaks as signal peaks. Thus, in accordance with the principles of the present invention, a noise threshold for the received signals is first determined. In the above referenced patent application the noise threshold was determined from the characteristics of a sequence of received Doppler signals. This technique requires an initial signal acquisition period to determine the noise threshold, and hence the clinician must wait for this period before accurate information is available. The technique of the present invention, by contrast, determines the threshold from known system or transducer performance parameters, enabling the noise threshold to be predetermined and hence immediately available when Doppler signal acquisition begins. Accurate peak velocity information is therefore immediately available.

Figure 3:
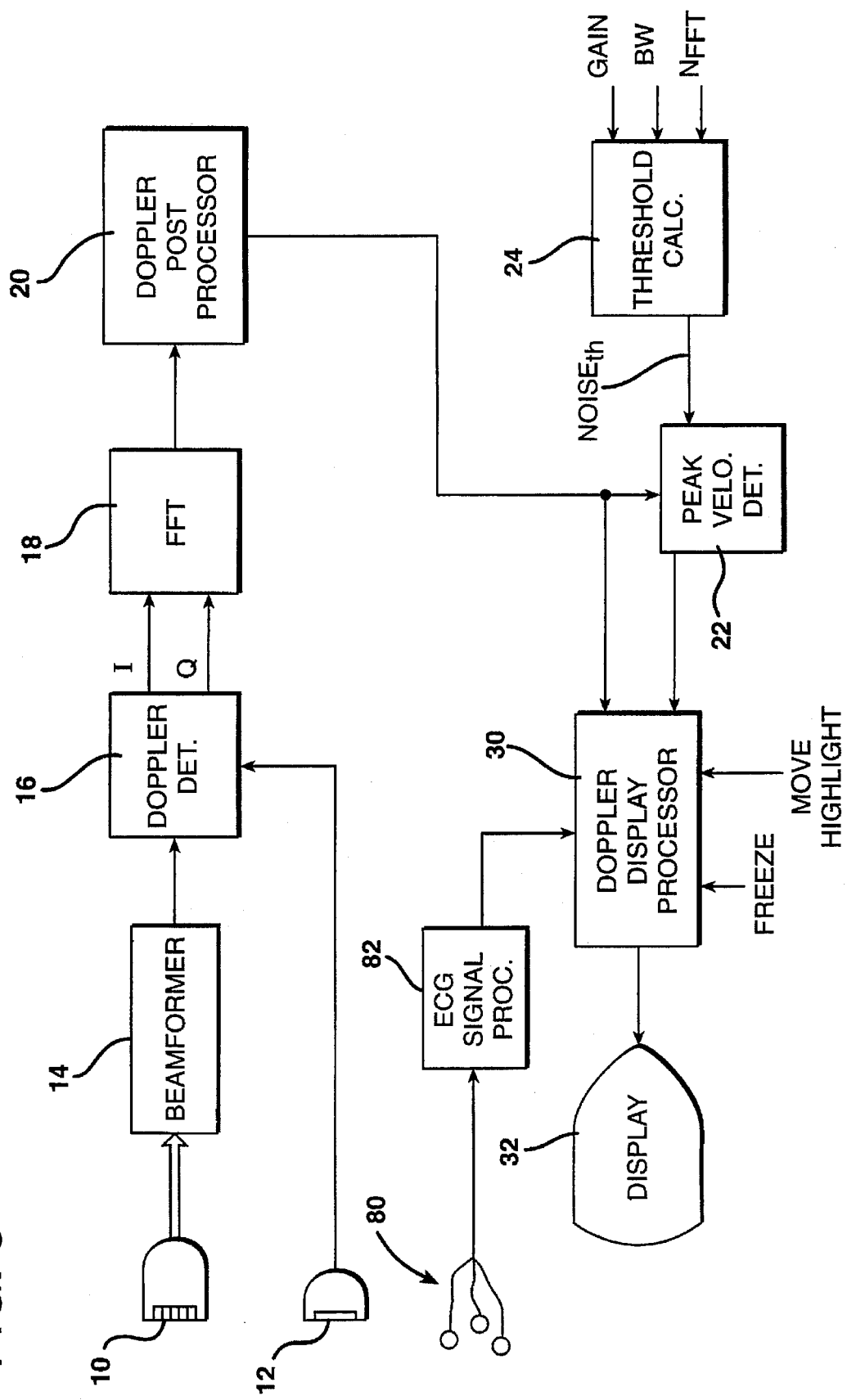
FIG. 3 is a block diagram of ultrasonic Doppler processing apparatus which identifies the peak velocity of a spectral line in accordance with the principles of the present invention.

Referring concurrently to FIG. 3, a block diagram of an ultrasonic Doppler processing system which identifies the peak velocity of a spectral line in accordance with the principles of the present invention is shown. Doppler signals are received by an ultrasonic transducer 10 or 12. If the transducer is a multielement array transducer 10 the signals received by the multiple elements are formed into a single signal or beam by a beamformer 14. When a single element transducer 12 is used, beamforming is not necessary. The Doppler signal information is detected by a Doppler detector 16 which produces quadrature I and Q signal components. A number of such signal components from the site in the body being diagnosed are applied to a Doppler processor 18, one form of which is a fast Fourier transform (FFT) processor, which computes the Doppler frequency shift of the received signals. This basic Doppler data is post- (or pre-) processed by a Doppler post processor 20, which further refines the data by techniques such as wall filtering, gain control, or amplitude compression.

Figure 4:
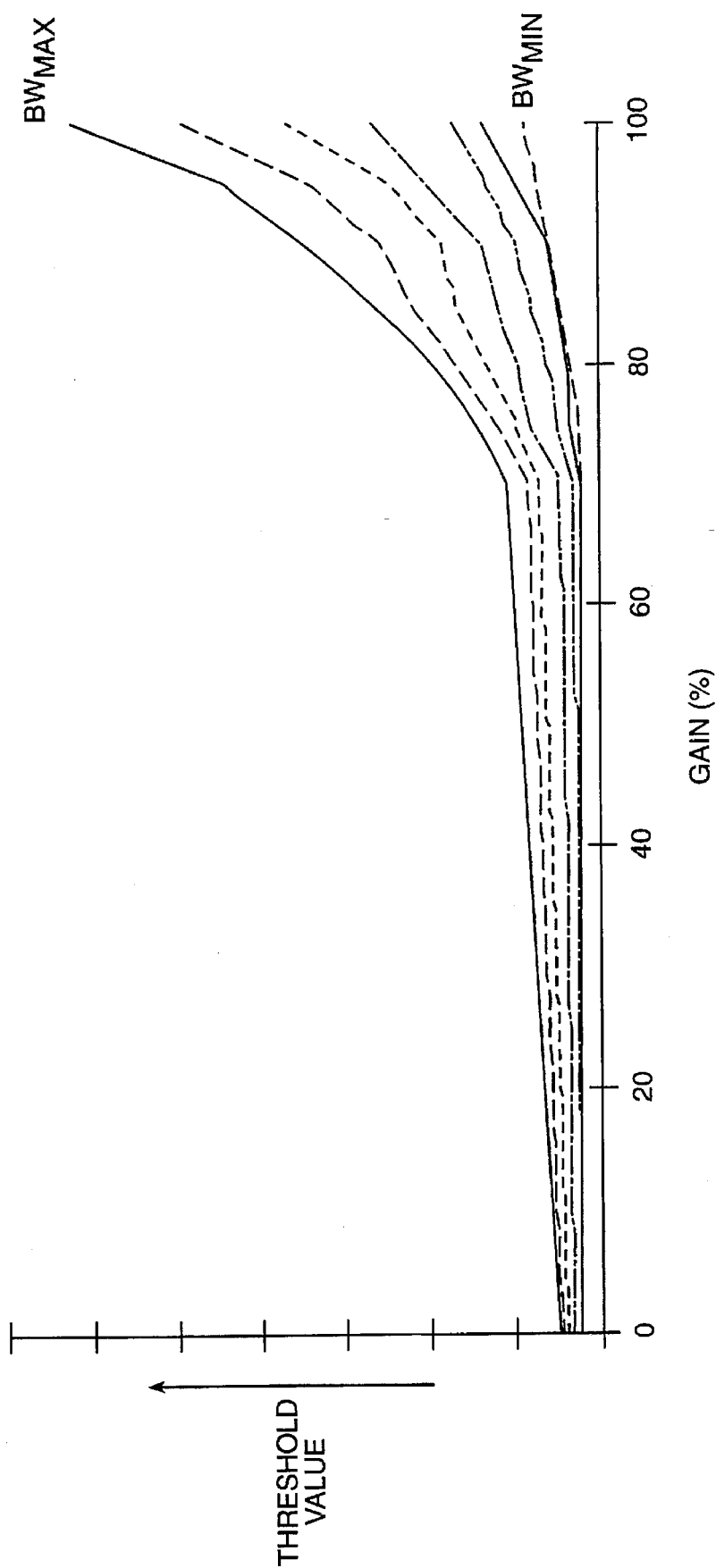
FIG. 4 illustrates a number of Doppler noise threshold levels plotted in accordance with the principles of the present invention.

The post processed Doppler data, now in a form as represented by the circles and X's of FIG. 1, is applied to a peak velocity detector 22 and a Doppler display processor 30. The Doppler display processor uses the Doppler data in the display of a real time sequence of spectral line information. The peak velocity detector compares the Doppler data against a noise threshold $NOISE_{th}$ to determine the peak velocity point of a spectral line, as discussed more fully below in the description of FIG. 2. The peak velocity detector may also perform filtering of the Doppler data. The noise threshold $NOISE_{th}$ is calculated by a threshold calculator 24 from a number of system operating parameters including gain, bandwidth, and the number of points (or bins or discrete Doppler gradation levels) of the Doppler processor. In the illustrated embodiment this would be the number of points of the FFT processor. A preferred algorithm is of the form $$NOISE_{th} = C_{proc} \sqrt{N_{FFT}} \sqrt{BW}\ F(gain)$$

where $C_{proc}$ is a constant depending upon system noise in the processing path of the selected transducer (e.g., single or multiple element transducer), $N_{FFT}$ is the number of points of the FFT processor, BW is the Doppler processing bandwidth, and F(gain) is a function depending on the gain applied to the Doppler signals. The noise threshold may also be weighted by other factors depending upon system operating performance, such as transducer aperture and other system or transducer parameters. FIG. 4 illustrates a typical variation of $NOISE_{th}$ with gain and bandwidth parameters, two parameters that are often determined by the settings of user controls. The number of points in the Doppler processor is usually fixed and not variable by the user. FIG. 4 graphically illustrates a family of curves for different bandwidth (BW) settings. A typical BWmax setting may be 20 KHz. Gain is shown in percentage of full gain value, and the noise threshold is indicated along the ordinate of the graph.

Since the noise threshold is dependent upon system or transducer characteristics which are known in advance of use of the system, noise threshold levels can be precalculated and stored in a memory device, then looked up and used depending upon the particular performance characteristics selected by the user for a given diagnostic procedure. For example the curves of FIG. 4 can be precomputed for both the array and single element transducers and stored in memory. When a user selects one of the transducers, the particular family of curves for that transducer is identified. When a user sets the Doppler processing system for a particular bandwidth, the threshold calculator 24 would select one of the curves of FIG. 4. A particular threshold level along the selected curve would be chosen and used by the threshold calculator depending upon the gain setting selected by the user. Thus, the threshold level can be computed in real time by the threshold calculator or chosen from a variety of precalculated and stored values.

Figure 2:
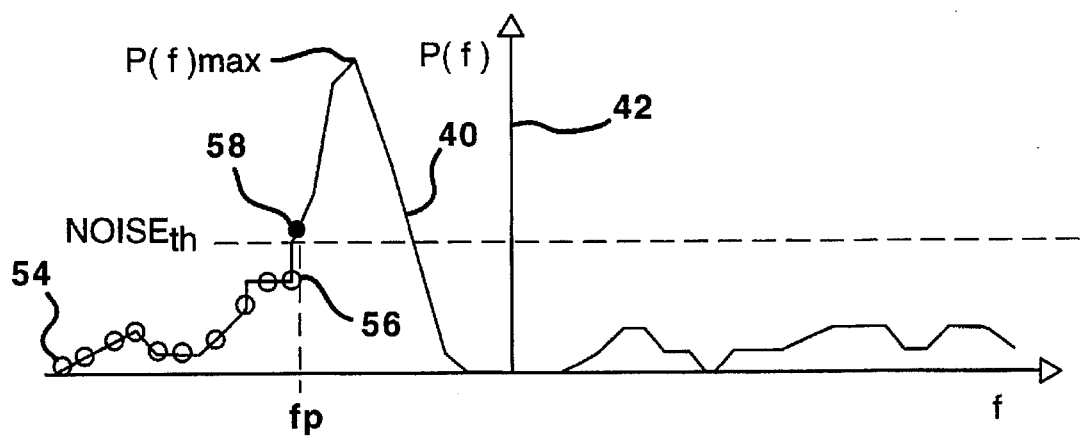
FIG. 2 illustrates the identification of the peak velocity of a spectral line in accordance with the principles of the present invention.

The comparison of the Doppler data against a noise threshold $NOISE_{th}$ by the peak velocity detector to determine the peak velocity point of the data is illustrated with reference to FIG. 2. First, the user selects a direction of blood flow to be used as a reference. This reference determines the end of the spectrum from which the search for the peak velocity is to proceed. In the exemplary spectral line of FIG. 2, it is assumed that the user has chosen a direction corresponding to the left side of the baseline 42, indicating flow toward (or away from, depending upon the chosen convention) the transducer. The search for the peak velocity value therefore begins from the leftmost digital value, which is circle 54.

Figure 5:
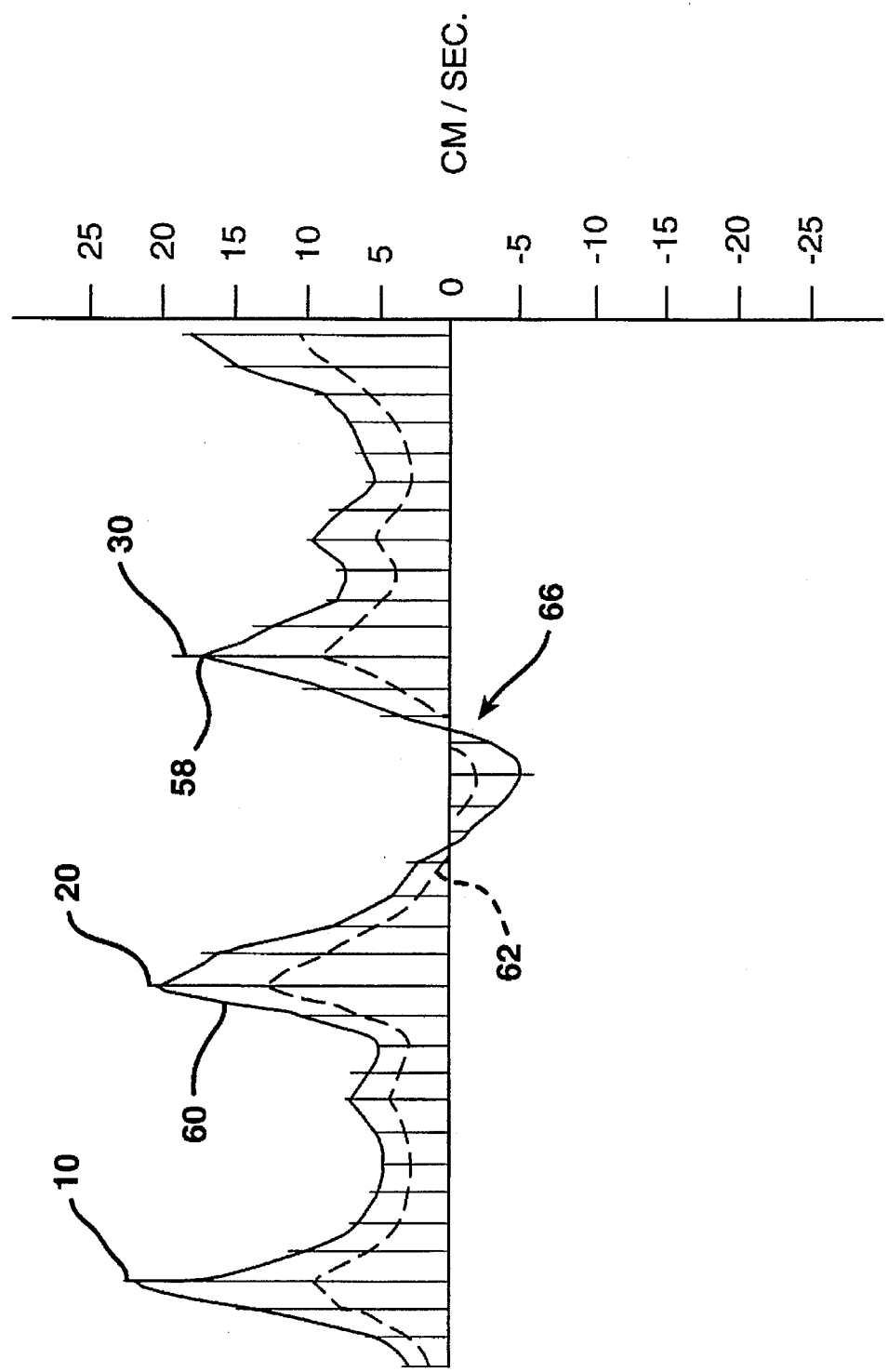
FIG. 5 illustrates a continuous scrolling display of spectral Doppler peak and mean velocities in accordance with the principles of the present invention.

The search for the peak velocity value proceeds from value 54 and continues to the right in the drawing, through value 56 and then to the value indicated by the solid circle 58. Between values 56 and 58 the $NOISE_{th}$ threshold is traversed. The peak velocity detector 22 will choose the value closest to the $NOISE_{th}$ threshold as the peak velocity value, which in the example shown is digital value 58. This value has a frequency of fp as shown in the drawing, which is substantially the highest frequency of the values which are above the $NOISE_{th}$ threshold. The velocity corresponding to fp is thus identified as the peak velocity for this spectral line, and that velocity is graphically marked in the spectral line display. FIG. 5 illustrates a spectral line display in which the peak velocity of each spectral (vertical) line has been identified in this manner and the peaks connected by the solid display line 60. As FIG. 5 shows, the spectral line peak velocities can be identified and displayed as the spectral lines occur and are displayed, thereby providing a real time continuous display of peak spectral velocities.

For each displayed spectral line a mean velocity value can be calculated and displayed. A variety of techniques are known for calculating mean velocity, a preferred one being an intensity weighted mean of the spectral P(f) digital values. The mean velocity thereby determined may be marked on the spectral line display, also concurrently with the initial appearance of the spectral line at the right-hand side of the spectral line display. FIG. 5 shows a dashed line display which connects the calculated mean velocity values of the displayed spectral lines.

The spectral display of FIG. 5 typically scrolls in real time across the display monitor 32 from right to left across the screen. New spectral lines are continually appearing at the right side of the display, and old lines from previous heart cycles disappear as they reach the left side of the display. In the example of FIG. 5, each spectral line indicates the range of flow velocities existing at that moment at the diagnostic site in the heart being examined.

Figure 6A:
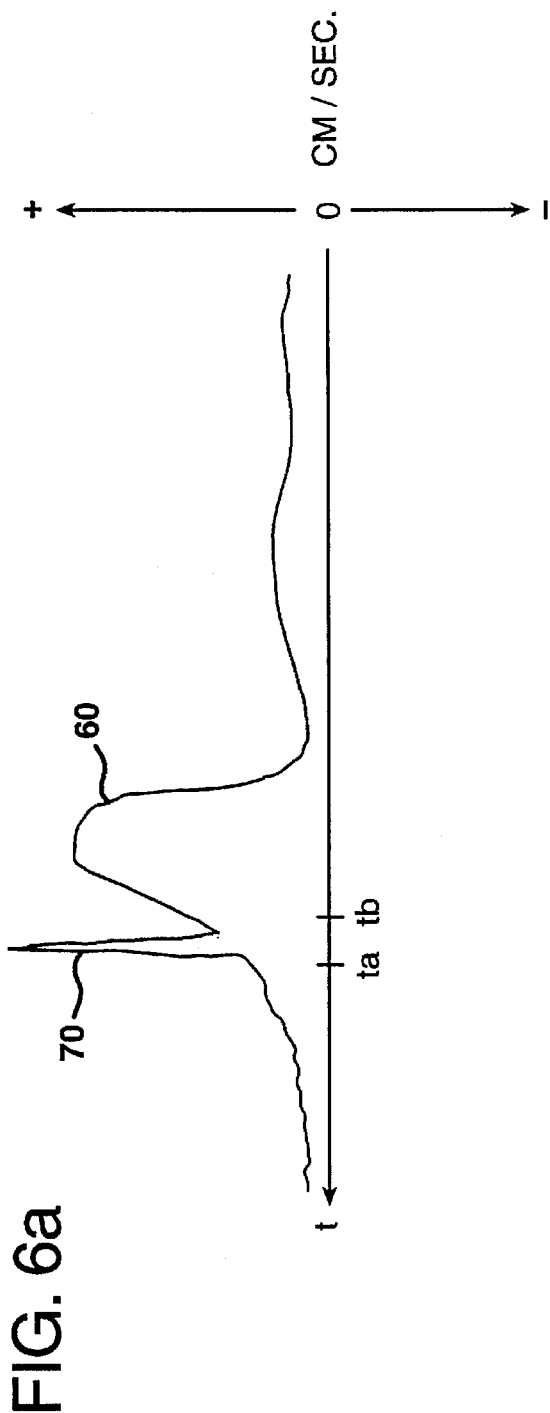
FIGS. 6a and 6b illustrate the elimination of a valve click artifact from a cardiac Doppler display in accordance with the principles of the present invention.
Figure 6B:
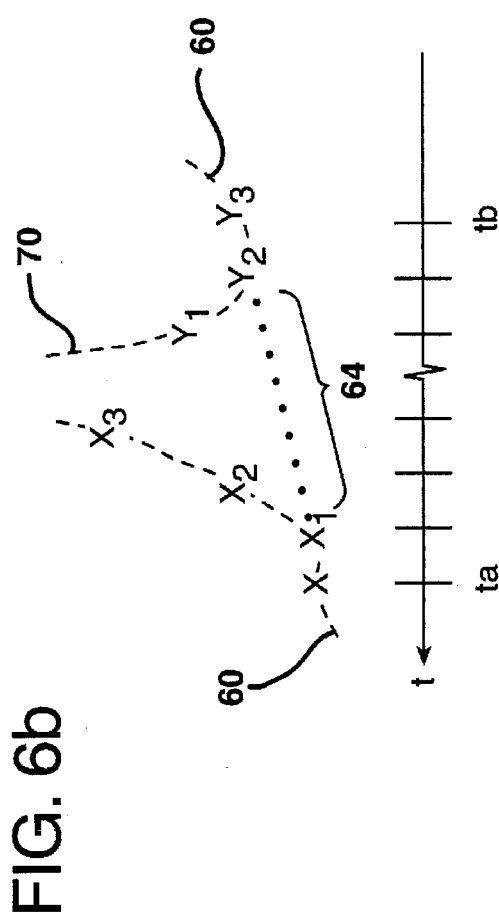

FIGS. 6a and 6b illustrate the removal of valve click artifacts in accordance with the principles of the present invention. FIG. 6a illustrates the technique with reference to a smooth trace 60 of the spectral line peak velocity values. The trace 60 is seen to contain a high amplitude spike 70, as might appear in the data as a result of detection of a valve click. The artifact 70 occurs between the times $t_a$ and $t_b$ of two of the spectral lines of the data. These times are shown on the horizontal axis of FIG. 6b, along with a number of intervening times t at which spectral lines occur. In FIG. 6b the peak velocities of successive spectral lines are indicated by X's and Y's and are interconnected by the trace 60 and the outline of the artifact spike 70. In this example the artifact begins with the sudden increment in peak velocity between values $X_1$ and $X_2$, and continues with point $X_3$. When this increment exceeds a given amount over a given number of spectral lines, the onset of the artifact spike 70 has been detected. This measure could be an increment of ten gradation levels (or bins or points) of the quantization levels of the Doppler data over an interval of one or two spectral lines, for example. Alternatively the increment can be specified as a percentage of the full range of quantization such as 10%. Increments in excess of this measure are identified as the onset of an artifact by the Doppler display processor 30 from an examination of a sequence of spectral lines prior to their display on the display 32.

Similarly in this example, a sudden decrement of ten gradation levels over one or two spectral line intervals can be taken to signal the decline of the artifact spike, with the spike ending when the decrement between lines declines to three gradation levels or less. In FIG. 6b, such a decline is realized between artifact ending points $Y_2$ and $Y_3$, as the sharply decrementing peak values Y pass through an inflection point and once again proceed to follow the smooth path of the trace 60.

In this example the Doppler display processor would identify point $X_1$ as the start of the artifact 70 and point $Y_2$ as the end of the artifact. The artifact is then eliminated by displaying interpolated values over the artifact interval. In this example the interpolated points indicated by dots 64 between the artifact end points are linearly interpolated from the end point data and used for spectral display in place of Doppler values received during the artifact 70.

Those skilled in the art will recognize that valve click artifacts can be of either polarity in the spectral display. For a negative going artifact the onset of the artifact will be indicated by an excessive decrement in gradation level, and its termination will be indicated by a subsequent excessive increment in level.

It has been found that when the velocity range of the spectral line is close to the horizontal baseline, as indicated in the vicinity 66 of the spectral line display of FIG. 5, the spectral line data is more greatly influenced by tissue motion effects and hence is erratic. To account for this, the increment and decrement measures may be increased (e.g., from 10% to a greater percentage) as the peak velocity values approach the baseline, which prevents the replacement of received data values which are otherwise of interest to the clinician.

Thus, by examining the data of a sequence of spectral lines prior to its display, the Doppler display processor 30 is able to detect the onset and ending of an artifact prior to its display, and replace the artifact with interpolated data values for display.

Figure 7:
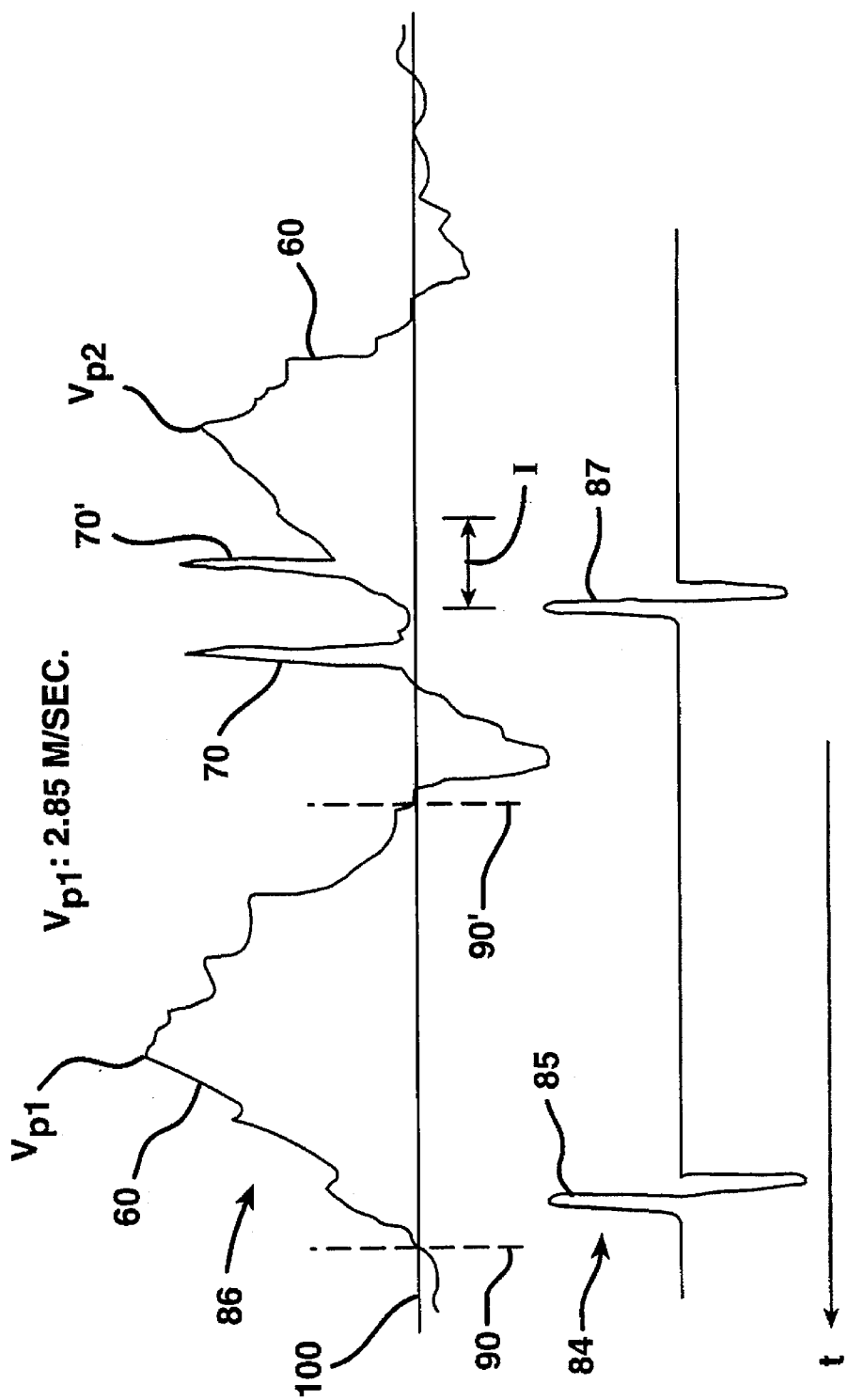
FIG. 7 illustrates the determination of the peak blood flow velocity during a cardiac cycle using a measured R-wave signal.

A cardiac Doppler signal processor will desirably calculate and display parameters for each or a selected heart cycle, such as peak velocity and peak gradient. These calculations are relatively easily calculated in the cardiovascular system outside the heart, as the spectral display generally presents a clear delineation of separate cardiac cycles. However, when the heart itself is being examined, the spectral data can exhibit a great variety of shapes and variations due to the presence of arrhythmia, valve clicks, and other extraneous factors. In accordance with a further aspect of the present invention, these cyclic determinations are more reliably produced by defining a heart cycle of the spectral data from the heart's R-wave signal. The R-wave is the electrical physiological signal produced to stimulate the heart's contraction, and is conventionally detected by an electrocardiograph (ECG). FIG. 3 shows a set of ECG electrodes 80 which may be affixed to the chest of a patient to detect the R-wave signal. The signal is detected and processed by an ECG signal processor 82 and applied to the Doppler display processor 30, which displays the ECG waveform 84 in synchronism with the scrolling spectral Doppler display 86. Referring to FIG. 7, the data in the interval between R-waves, such as the spectral lines existing between R-waves 85 and 87, delineates one heart cycle and is used to determine a single set of cyclic heart measurements such as the peak velocity and peak gradient occurring during one heart cycle. Thus, these measurements are more greatly immune to wide variations in the character of the spectral data. The peak velocity $V_{P1}$ and $V_{P2}$ occurring during each heart cycle can be taken as the first major peak in the trace 60 which follows the R-wave 85, 87 by at least a given interval I. As valve clicks are more likely to occur in the vicinity of the R-wave as the heart is stimulated to contract, this peak velocity detection technique can prevent a valve click artifact such as 70 or 70' from being erroneously identified as the peak velocity in the heart cycle.

In accordance with a further aspect of the present invention, the Doppler information of a delineated heart cycle is processed to compute quantified, numerical measures of cardiac performance such as the peak blood flow velocity, peak pressure gradient, the velocity time integral, the time averaged peak velocity, and mean pressure gradient, for instance. The peak blood flow velocity identified during a heart cycle might be displayed numerically aside the spectral display as 2.85 meters/second, for example. The display processor of the present invention affords the user with an instant visual indication of the relationship of the quantified display values to the spectral display by highlighting the spectral lines corresponding to the cardiac interval over which the quantified values were determined. While viewing a real time display of spectral and quantified information the user may at any time press the "freeze" button to freeze the display on the screen. The display might at that moment be displaying a peak velocity value of 2.85 m/sec as shown in FIG. 7. The display processor will indicate the cardiac interval over which this peak value was determined by automatically highlighting a portion of the spectral display between vertical lines 90, 90'. The user will thus know that the displayed peak velocity measure of 2.85 m/sec was determined from the same interval of Doppler data that was used to form the spectral lines between the vertical highlights 90, 90'.

In a preferred embodiment the user is able to manually relocate the automatically placed highlights 90, 90' along the time (horizontal) axis. This permits the user to manually adjust the automatically determined interval to a uniquely user determined interval. Once the highlight lines 90, 90' are relocated to new positions, the processor automatically recomputes new quantified display values based on the Doppler information of the newly selected interval.

This same highlighting technique may be employed as the spectral lines are scrolled in real time, in which case the highlighted spectral lines would proceed across the monitor. Instead of vertical lines 90, 90', the spectral lines themselves could be highlighted as by displaying the spectral lines of the corresponding interval in a different color, hue, or brightness from the surrounding lines.

In the case of erratic cardiac spectral displays the display processor might simply align the highlighted spectral lines and the quantification interval with the R-wave signals. The spectral line interval could in such instance be highlighted by color or intensity modulation of the corresponding interval of an R-wave waveform which is spatially aligned with the spectral waveform as in FIG. 7. For more stable displays in other regions of the cardiovascular system the delineated interval might be determined from the spectral data itself, as by delineating a region between successive baseline crossovers, indicated by the intersection of the waveform 60 in FIG. 7 with the baseline 100. As a new complete cardiac cycle scrolls into view, the highlighted area of the spectral display shifts in synchronism with the display of new quantified values calculated over the newly displayed heart cycle.

In analysis systems of the prior art, clinicians were required to freeze a display, then manually place cursors over the spectral image to delineate the portion of the cycle over which measurements were to be computed. In an embodiment of the present invention such manual efforts are obviated by the automatic operation of the display system to highlight the spectral lines corresponding to the heart cycle interval over which the quantified display values were produced or pertain.

What is claimed is:

1. Ultrasonic diagnostic imaging apparatus for providing Doppler information concerning blood flow velocities within a body comprising:

a transducer for acquiring Doppler signals from a site within the body;

an ultrasonic Doppler signal processing system coupled to receive Doppler signals from said transducer including means for processing said Doppler signals to produce spectral line data for continuous display of a succession of spectral lines indicating blood flow velocities during Doppler signal acquisition;

means for producing a threshold level which is a function of operating characteristics of said system or of said system and said transducer;

means for utilizing said threshold level and said spectral line data to identify a peak velocity value of a spectral line prior to the display of the spectral line; and means for displaying a sequence of said spectral lines and their identified peak velocity values substantially in real time.

2. The ultrasonic diagnostic imaging apparatus of claim 1, wherein said means for producing a threshold level produces a threshold level which is a function of signal gain, bandwidth, and a characteristic of said Doppler signal processing means.

3. The ultrasonic diagnostic imaging apparatus of claim 2, wherein said Doppler signal processing means includes a fast Fourier transform processor, and wherein said characteristic of said Doppler signal processing means comprises the number of points of said processor.

4. The ultrasonic diagnostic imaging apparatus of claim 3, wherein said means for producing a threshold level computes a threshold level from an equation of the form $NOISE_{th}=C_{proc}\sqrt{N_{FFT}}\sqrt{BW} F(gain)$, where $C_{proc}$ is a constant depending upon system noise in the processing path of the said transducer, $N_{FFT}$ is the number of points of said fast Fourier transform processor, BW is the Doppler processing bandwidth, and F(gain) is a function depending on the gain applied to the received Doppler signals.

5. The ultrasonic diagnostic imaging apparatus of claim 1, wherein the spectral line data relating to a spectral line comprise a plurality of data values exhibiting intensity and blood flow direction characteristics, and wherein said peak velocity value identifying means identifies the highest velocity value of said spectral line data values which exhibits a predetermined intensity relationship to said threshold level.

6. The ultrasonic diagnostic imaging apparatus of claim 5, wherein said identified peak velocity value is within a range of data values exhibiting blood flow directions that are within 180° of a user selected blood flow direction.

7. Ultrasonic diagnostic imaging apparatus for providing Doppler information concerning blood flow velocities within a body comprising:

a transducer for acquiring Doppler signals from a site within the body;

an ultrasonic Doppler signal processing system coupled to receive Doppler signals from said transducer including a fast Fourier transform processor for processing said Doppler signals to produce spectral line data for continuous display of a succession of spectral lines indicating blood flow velocities during Doppler signal acquisition;

a threshold level calculator which produces a threshold level that is a function of operating characteristics of said system or of said system and said transducer; a detector responsive to said threshold level and said spectral line data which identifies a peak velocity value of a spectral line prior to the display of the spectral line; and a display which displays a sequence of said spectral lines and their identified peak velocity values substantially in real time.

8. The ultrasonic diagnostic imaging apparatus of claim 7, wherein said threshold level calculator includes a storage device which stores a plurality of selectable threshold levels representing threshold levels for different user selectable system or system and transducer characteristics.

9. The ultrasonic diagnostic imaging apparatus of claim 8, wherein said threshold level is a function of a characteristic of said fast Fourier transform processor, Doppler signal bandwidth, and the gain applied to said Doppler signals in said system.

10. The ultrasonic diagnostic imaging apparatus of claim 1, further comprising:

means for identifying large amplitude artifacts in said spectral line data prior to display of spectral lines affected by said artifacts; and means for preventing the display of the peak velocities of said identified large amplitude artifacts.

11. The ultrasonic diagnostic imaging apparatus of claim 10, wherein said identifying means comprises means for identifying amplitude variations in peak velocity values of said spectral line data which are characteristic of the onset and conclusion of an artifact.

12. The ultrasonic diagnostic imaging apparatus of claim 11, wherein said amplitude variations are in units of velocity gradation of said spectral line data.

13. The ultrasonic diagnostic imaging apparatus of claim 11, wherein said preventing means comprises means for interpolating data values to be displayed in place of the peak velocity values of said large amplitude artifacts.

14. Ultrasonic diagnostic imaging apparatus for providing Doppler information concerning blood flow velocities within a body comprising:

a transducer for acquiring Doppler signals from a site within the body;

an ECG detector for detecting the R-wave signal of the heart and producing R-wave timing information;

an ultrasonic Doppler signal processing system coupled to receive Doppler signals from said transducer and said R-wave timing information, including means for processing said Doppler signals to produce spectral line data for continuous display of a succession of spectral lines indicating blood flow velocities during Doppler signal acquisition; and means for utilizing said R-wave timing information and said spectral line data to determine a time interval of spectral line data from which a cardiovascular characteristic is to be determined.

15. The ultrasonic diagnostic imaging apparatus of claim 14, wherein said utilizing means further comprises means for determining a time interval of spectral line data corresponding to one heart cycle.

16. The ultrasonic diagnostic imaging apparatus of claim 15, wherein said utilizing means further comprises means for determining the peak blood flow velocity of a heart cycle, including means for inhibiting artifacts occurring within a predetermined time interval of the occurrence of an R-wave from being identified as peak blood flow velocity values.

17. Ultrasonic diagnostic imaging apparatus for providing Doppler information concerning blood flow velocities within a body comprising:

a transducer for acquiring Doppler signals from a site within the body;

an ultrasonic Doppler signal processing system coupled to receive Doppler signals from said transducer and said R-wave timing information, including means for processing said Doppler signals to produce spectral line data;

a video display responsive to said spectral line data for displaying a succession of spectral lines substantially in real time;

means responsive to said spectral line data for producing one or more quantified measures of cardiovascular performance; and wherein said system further includes means for automatically visually designating the displayed spectral lines corresponding to said quantified measures.

18. The ultrasonic diagnostic imaging apparatus of claim 17, wherein said means for automatically visually designating comprises means for highlighting the displayed spectral lines corresponding to said quantified measures.

19. The ultrasonic diagnostic imaging apparatus of claim 18, wherein said highlighting means comprises means for highlighting, by modulation of color, hue, or brightness, the displayed spectral lines corresponding to said quantified measures.

20. The ultrasonic diagnostic imaging apparatus of claim 17, further comprising means for delineating a sequence of spectral lines corresponding to one heart cycle, wherein said quantified measure producing means is further responsive to the delineation of a heart cycle for producing a quantified measure from spectral line data corresponding to said delineated heart cycle, and wherein said means for automatically visually designating the displayed spectral lines corresponding to said quantified measures comprises means for highlighting the spectral lines corresponding to the spectral line data from which said quantified measure was produced.

21. The ultrasonic diagnostic imaging apparatus of claim 20, wherein said means for delineating a sequence of spectral lines corresponding to one heart cycle comprises an ECG detector.

22. The ultrasonic diagnostic imaging apparatus of claim 17, wherein said means for visually designating comprises means for automatically visually designating the displayed spectral lines corresponding to said quantified measures while said spectral lines are displayed substantially in real time.

23. The ultrasonic diagnostic imaging apparatus of claim 17, further comprising means for manually changing the displayed spectral lines which are visually designated by said means for automatically visually designating;

wherein said means for producing quantified measures is further responsive to said manually changing means for producing quantified measures corresponding to a change in said visually designated spectral lines.

24. In an ultrasonic diagnostic imaging system for diagnosing cardiovascular performance, a method for simultaneously displaying spectral Doppler data and quantified measures of cardiovascular performance comprising:

receiving ultrasonic Doppler signals from the cardiovascular system of a person;

processing said ultrasonic Doppler signals to produce a spectral Doppler display;

processing said ultrasonic Doppler signals to produce quantified measures of cardiovascular performance for simultaneous display with said spectral Doppler display; and automatically visually designating a portion of said spectral Doppler display which corresponds to the ultrasonic Doppler signals from which said quantified measures were produced.

25. The method of claim 24, further comprising receiving signals from said person which delineate one heart cycle;

wherein the step of processing processes ultrasonic Doppler signals corresponding to a delineated heart cycle; and wherein the step of automatically visually designating designates a portion of said spectral Doppler display which corresponds to said delineated heart cycle.

* * * * *